(12) United States Patent
Lange

(10) Patent No.: US 10,126,251 B2
(45) Date of Patent: *Nov. 13, 2018

(54) INSPECTION SYSTEMS AND TECHNIQUES WITH ENHANCED DETECTION

(71) Applicant: KLA—Tencor Corporation, Milpitas, CA (US)

(72) Inventor: Steven R. Lange, Alamo, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/451,990

(22) Filed: Mar. 7, 2017

(65) Prior Publication Data

US 2017/0176346 A1 Jun. 22, 2017

Related U.S. Application Data

(63) Continuation of application No. 14/944,124, filed on Nov. 17, 2015, now Pat. No. 9,599,573.

(Continued)

(51) Int. Cl.
*G01N 21/95* (2006.01)
*G01N 21/88* (2006.01)
(Continued)

(52) U.S. Cl.
CPC ..... *G01N 21/9505* (2013.01); *G01N 21/8806* (2013.01); *G01N 21/9501* (2013.01);
(Continued)

(58) Field of Classification Search
CPC ........ G03F 7/70633; G01N 2021/8845; G01N 21/956; G01N 21/9501
(Continued)

(56) References Cited

U.S. PATENT DOCUMENTS 5,162,867 A * 11/1992 Kohno .................. G01N 21/94
356/237.5
6,608,321 B1 8/2003 La Fontaine et al.
(Continued)

FOREIGN PATENT DOCUMENTS

CN 102288550 A 12/2011
JP 2008294249 A 12/2008
(Continued)

OTHER PUBLICATIONS

"U.S. Appl. No. 14/944,124, Notice of Allowance dated Nov. 4, 2016", 10 pages.
(Continued)

*Primary Examiner* — Roy M Punnoose
(74) *Attorney, Agent, or Firm* — Kwan & Olynick LLP

(57) ABSTRACT

Disclosed are methods and apparatus for inspecting semiconductor samples. On an inspection tool, a plurality of different wavelength ranges is selected for different layers of interest of one or more semiconductor samples based on whether such different layers of interest have an absorber type material present within or near such different layers of interest. On the inspection tool, at least one incident beam is directed at the different wavelength ranges towards the different layers of interest and, in response, output signals or images are obtained for each of the different layers of interest. The output signals or images from each of the different layers of interest are analyzed to detect defects in such different layers of interest.

16 Claims, 5 Drawing Sheets

Related U.S. Application Data

(60) Provisional application No. 62/086,596, filed on Dec. 2, 2014.

(51) Int. Cl.
*G01N 21/956* (2006.01)
*G03F 7/20* (2006.01)

(52) U.S. Cl.
CPC ......... *G01N 21/956* (2013.01); *G03F 7/7065* (2013.01); *G03F 7/70633* (2013.01); *G01N 2021/8845* (2013.01); *G01N 2021/8848* (2013.01)

(58) Field of Classification Search
USPC ...................................................... 356/237.5
See application file for complete search history.

(56) References Cited

U.S. PATENT DOCUMENTS

| | | | |
|---|---|---|---|
| 8,137,872 | B2 | 3/2012 | Hayashi |
| 8,896,827 | B2 | 11/2014 | Chimmalgi et al. |
| 9,599,573 | B2* | 3/2017 | Lange ................ G01N 21/8806 |
| 2004/0095573 | A1 | 5/2004 | Tsai et al. |
| 2004/0130727 | A1 | 7/2004 | Isozaki et al. |
| 2004/0207836 | A1 | 10/2004 | Chhibber et al. |
| 2006/0219930 | A1 | 10/2006 | Lange |
| 2006/0281028 | A1 | 12/2006 | Peng et al. |
| 2007/0058164 | A1* | 3/2007 | Shibata ............ G01N 21/95607 356/237.2 |
| 2007/0138414 | A1* | 6/2007 | Stevens .................. G01N 21/94 250/504 R |
| 2010/0302360 | A1 | 12/2010 | Arai et al. |
| 2012/0046884 | A1 | 2/2012 | Oka et al. |
| 2012/0287263 | A1 | 11/2012 | Zhou |
| 2013/0114880 | A1* | 5/2013 | Matsumoto .......... G01B 11/303 382/149 |
| 2014/0139830 | A1 | 5/2014 | Lange |
| 2014/0268105 | A1 | 9/2014 | Bills et al. |
| 2016/0153914 | A1 | 6/2016 | Lange |

FOREIGN PATENT DOCUMENTS

| | | |
|---|---|---|
| JP | 2010245165 A | 10/2010 |
| WO | 2011008964 A1 | 1/2011 |

OTHER PUBLICATIONS

"International Application Serial No. PCT/US2015/063020, Search Report dated Feb. 25, 2016", 3 pages.

International Search Report for application No. 11201704382X, application filed Nov. 30, 2015, Search Report completed Mar. 5, 2018.

Written Opinion Application No. 11201704382X, Application filed Nov. 30, 2015. Date of Written Opinion dated Jul. 5, 2018.

* cited by examiner

INSPECTION SYSTEMS AND TECHNIQUES WITH ENHANCED DETECTION

CROSS-REFERENCE TO RELATED APPLICATION

This application is a continuation of and claims the benefit under 35 U.S.C. § 120 of U.S. application Ser. No. 14/944,124, filed 17 Nov. 2015, now issued as U.S. Pat. No. 9,599,573 on 21 Mar. 2017, which claims priority to U.S. Provisional Patent Application No. 62/086,596, filed 2 Dec. 2014. Both applications are incorporated herein by reference in their entireties for all purposes.

TECHNICAL FIELD OF THE INVENTION

The invention generally relates to the field of wafer inspection systems. More particularly the present invention relates to defect detection using shorter wavelengths.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to detects. That is, detects which cause faults in the device are becoming increasingly smaller. The device needs to be generally fault free prior to shipment to the end users or customers.

Various inspection systems are used within the semiconductor industry to detect defects on a semiconductor wafer. However, there is a continued demand for improved semiconductor wafer inspection systems and techniques.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method for inspecting semiconductor samples is disclosed. On an inspection tool, a plurality of different wavelength ranges is selected for different layers of interest of one or more semiconductor samples based on whether such different layers of interest have an absorber type material present within or near such different layers of interest. On the inspection tool, at least one incident beam is directed at the different wavelength ranges towards the different layers of interest and, in response, and output signals or images are obtained for each of the different layers of interest. The output signals or images from each of the different layers of interest are analyzed to detect defects in such different layers of interest.

In a specific implementation, the absorber type material is SiN. In one aspect, selecting the different wavelength ranges comprises (i) selecting a shorter wavelength range that is below an absorption edge wavelength of SiN for a first one of the different layers of interest that does not have SiN present within or near such first layer of interest or has SiN present below such first layer of interest, and (ii) selecting a longer wavelength range that is above the absorption edge wavelength for a second one of the different layers of interest that has SiN present above such second layer of interest. In a further aspect, selecting the different wavelength ranges further comprises selecting a narrow and shorter wavelength range at a third one of the different layers of interest that has SiN present within such third layer of interest. In a further aspect, the shorter wavelength range is 220 nm or less; the longer wavelength range is 230 nm or more; and the narrow and shorter wavelength range is between about 230 nm and 250 nm.

In another embodiment, selecting the different wavelength ranges includes determining whether there is SiN present within or near each of the different layers of interest as specified in a design database with which the sample was fabricated. In another aspect, selecting the different wavelength ranges includes determining whether there is SiN present within or near each of the different layers of interest as specified with a list of layers and material type without provision of a design database with which the sample was fabricated. In another implementation, a horizontal or vertical polarization is applied to the at least one incident beam. In another example, different aperture settings are selected for the at least one incident beam to achieve a particular angle of incidence for at least some of the different layers of interest. In an alternative embodiment, at least some of the different wavelength ranges for a particular layer of interest having a vertical stack structure include a longer wavelength range to detect defects on both a surface and throughout a depth of the vertical stack structure and a shorter wavelength range to detect defects on the surface of the vertical stack structure.

In an alternative embodiment, the invention pertains to an inspection system for inspecting a semiconductor sample. The system includes an illumination optics module for generating and directing an incident beam towards one or more semiconductor sample at a plurality of different wavelength ranges for different layers of interest based on whether such different layers of interest have an absorber type material present within or near a layer of interest at such different layers of interest. The system also includes a collection optics module for collecting an output beam that is reflected or scattered from the different layers of interest in response to the incident beam and a controller that is configured for performing one or more of the above-described methods.

These and other aspects of the invention are described further below with reference to the figures.

DETAILED DESCRIPTION OF EXAMPLE EMBODIMENTS

Figure 1A:
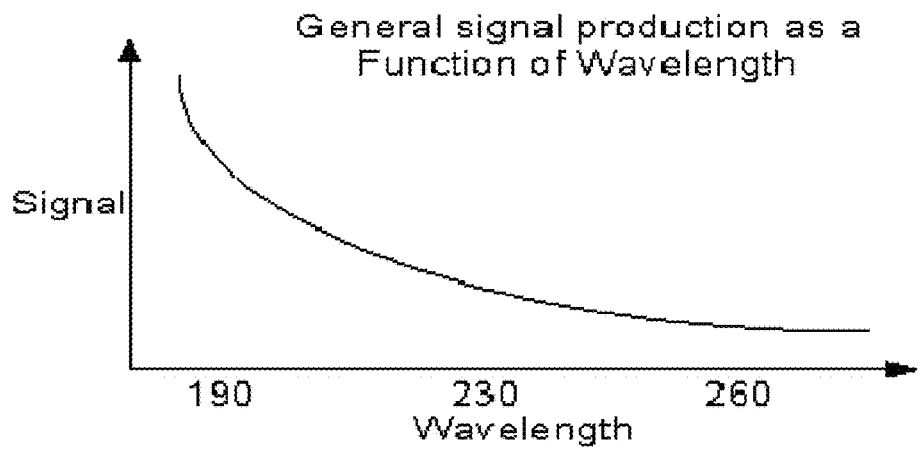
FIG. 1A is a graph of signal strength as a function of wavelength.

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with these specific embodiments, it will be understood that it is not intended to limit the invention to these embodiments.

The conditions can generally be optimized during wafer inspection for achieving the best signal to noise ratio (SNR) from a defect in a wafer structure. The detected signal from a defect area at a specific wafer location may be compared to a corresponding reference area in which a defect is not present. First, the light or electromagnetic field (e-field) must reach the defect location in order to receive a response signal or light from the defect. The likelihood of the incident light reaching the detect is a function of the material properties of the materials surrounding the detect area. A defect that is surrounded or located below an opaque material may have severe limits on the amount of light that can reach such defect, while transparent materials allow light to more likely reach such defect. A larger change in the n,k material properties (or refractive index n and extinction coefficient k) will tend to have a larger detected signal, which can more effectively be compared or analyzed for detect detection. Generally, signals are a function of the square of the permittivity, which is $n\pm ik$ and a complex function. So, changing either n or k can affect the signal that is generated. Finally, at least a portion of the altered local e-field around the detect needs to generally be propagated to the top surface of the wafer and then collected by the entrance pupil of the collection optics of the wafer inspection tool for analysis purposes during inspection. The presence of opaque and transmitting materials in the vicinity of the defect will affect this collection process.

There are several factors which can adversely affect detection of defects. For instance, the presence of SiN, either near the defect or surrounding the defect, can affect the detected signal, sometimes in complicated ways. Process variation during the wafer fabrication process can also act as an unwanted noise as it is generally undesirable to measure these noise sources, which may obscure defect signals. These process variations occur at all steps in the fabrication process to a more or lesser degree and, hence, the associated noise sources are present in inspection of all wafer layers.

The presence of opaque material layers beneath a defect can lessen or eliminate noise sources from below such opaque layers. Thus, it may be desirable in some cases to have absorbing materials in the wafer structures that are being inspected, depending upon where the structures under test are located. Since SiN starts becoming opaque at wavelengths below 230 nm, the presence of SiN can help to limit wafer process variation noise in the inspection if a shorter wavelength than 230 nm is used.

Another general factor in wafer inspection is that shorter wavelengths tend to produce stronger signals for many layers or defects of interest. This effect comes from the Raleigh and Mie scattering theory in which the signal of a particle on a wafer is proportional to $s^6/\text{wavelength}^4$ so that, in general, shorter wavelengths produce more signal. That is, shorter wavelengths generally allow a more sensitive inspection. In general, more defect signal strength can generally be obtained at shorter wavelengths as long there are not any large material n and k property changes, which may occur in the presence of an absorbing type material. FIG. 1A is a graph of signal strength as a function of wavelength. Accordingly, shorter wavelengths may be used when the inspection area is not in the presence of absorbing materials.

Figure 1B:
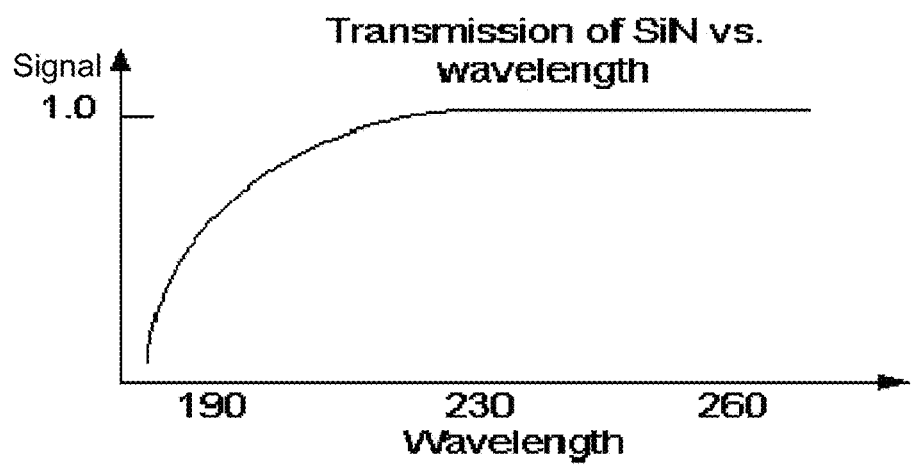
FIG. 1B is a graph illustrating signal transmission strength of SiN material.

However, specific material property changes for absorber type materials can outweigh the relationship between shorter wavelengths and strong signal strength in some cases. One common absorber material is SiN. SiN is often used throughout the semiconductor fabrication process as a hard mask, spacer, or memory (charge) storage medium. SiN has an optical property that is transparent to wavelengths greater than about 230 nm and gradually becomes opaque for wavelengths below that threshold with increasing absorption as wavelengths decrease. FIG. 1B is a graph illustrating signal transmission strength of SiN material. As shown, SiN (or other types of absorbing materials) becomes absorbing (i.e., opaque or less transmissive) at shorter wavelengths, such as below about 230 nm. Thus, if SiN is the layer of interest in an inspection, a longer wavelength is preferably used to achieve a stronger detected signal.

Figure 1C:
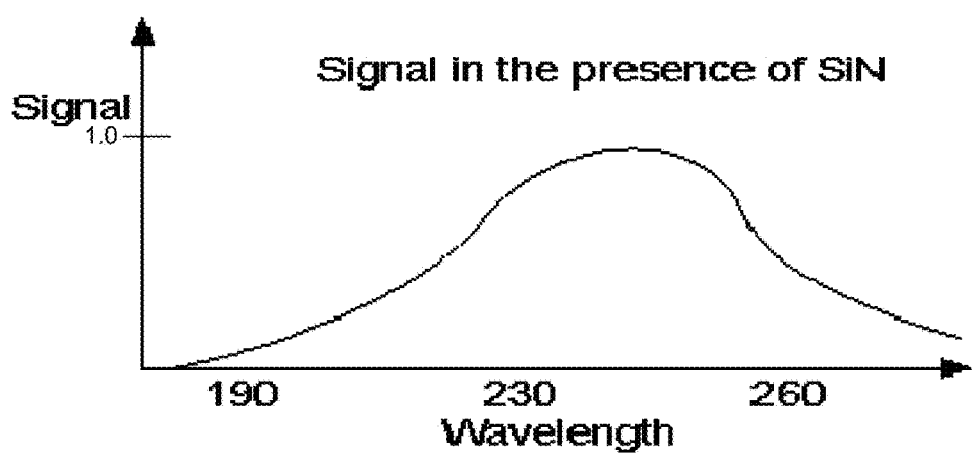
FIG. 1C is a graph illustrating signal strength for a detect in the presence of SiN material.

If SiN material is near a defect or layer of interest, this SiN presence may also affect the defect signal strength as illustrated in FIG. 1C. As shown, the signal peaks at around 245 nm. However, the signal for a defect in the presence of SiN (or other absorber materials) may peak at different wavelengths, depending on particular surrounding material properties and structures, as well as the defect's material properties and structure. The defect signal for other types of surrounding materials, such as oxides, may have a different peak position.

Thus, in some cases, it may be desirable to have wavelengths of inspection above 230 nm (or at a signal peak wavelength range) when SiN (other wavelength ranges for other material types) is involved. Having an inspector with a broadband spectrum that includes wavelengths above and below the absorption edge of about 230 nm from SiN is desirable to maximize the detected signal, which is dependent upon the materials that are present. Similarly, the presence of SiN can affect the noise that is detected in the inspection such that having wavelengths above and below the 230 nm absorption edge allows the most flexibility in maximizing the signal-to-noise ratio. Other absorption edges can be used to affect the wavelength selection in the presence of other types of material, besides SiN. Although the following embodiments are described in relation to the presence or absence of SiN, these techniques can be easily altered and applied to other absorber types of materials. Alternative example absorber materials, to which embodiments of the present invention may be applied, may include copper indium gallium diselenide (CIGS), CdTe amorphous silicon, $SiO_2$, etc.

In general, different wavelength ranges for different sample layers of interest are selected on an inspection tool based on whether such different layers of interest have an absorber type material, such as SiN, present within or near such layers of interest. On the inspection tool, the different wavelength ranges are directed towards the different layers of interest of one or more samples and, in response, output signals or images are collected from each of the different layers of interest. The collected output signals or images from each of the different layers of interest can then be analyzed to detect defects in such different layers of interest.

Figure 2:
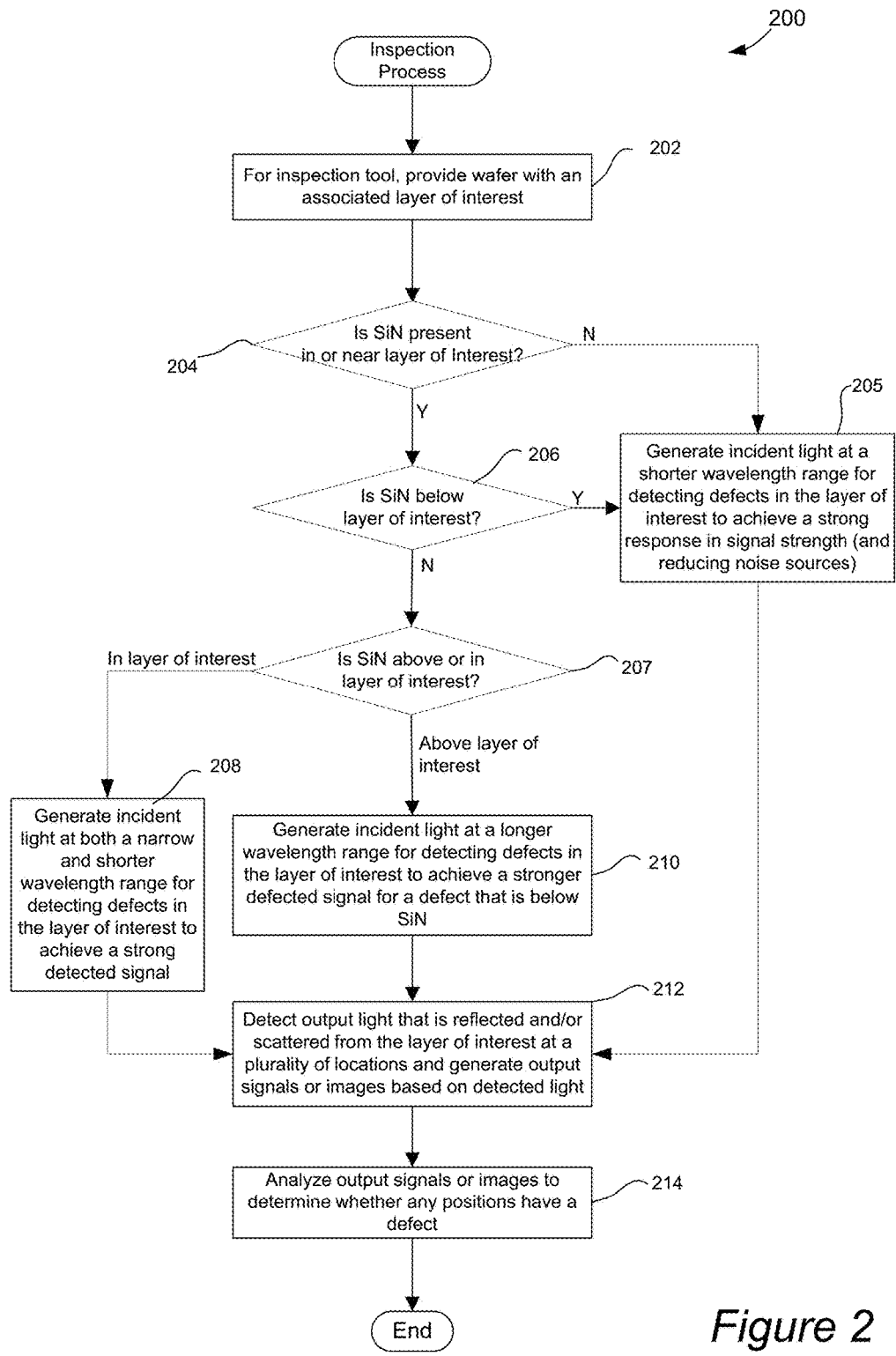
FIG. 2 is a flow chart illustrating an inspection process in accordance with one embodiment of the present invention.

FIG. 2 is a flow chart illustrating an inspection process 200 in accordance with one embodiment of the present invention. Initially, a wafer with an associated layer of interest may be provided for inspection in operation 202. For instance, the layer of interest may be comprised of SiN. For another wafer or layer of interest for a same wafer, SiN may be near the layer of interest, but not actually present in the layer of interest. In a specific example, the targets or structures of interest may be formed from materials other than SiN, but such targets or structures of interest may be located adjacent or near a structure having at least some SiN. Another wafer under test may contain SiN that is located under the layer of interest. Another wafer's layer of interest may not contain or be near SiN material or structures. In general, this inspection technique 200 may be repeated for different wafers with different or the same layers of interest or on different or the same layers of interest on the same wafer after different steps in the fabrication process have been performed.

In general, different wavelength ranges will be used for different layers of interest that have different SiN characteristics (or other absorber material characteristics) or lack thereof. For example, different wavelength and aperture combinations can be selected in the inspection tool for different layers of interest as described further herein.

In the illustrated example, it may be determined whether SiN is present in or near the layer of interest in operation 204. In one embodiment, the design database can be marked to specify which layers contain SiN, and such marked design database is provided to the inspection system. For instance, the design database can specify SiN locations relative to each inspected layer of the design. The presence of SiN may also be provided or determined by reviewing the GDS2 design file, which identifies materials that are used for each layer, and it may then be determined which layers contain SiN and whether these SiN layers are above or below or include each layer of interest. In another embodiment, a list of locations that contain SiN (e.g., locations are provided relative to the layer stack of a wafer) may be provided to the inspection system without providing the design database.

If SiN is not present in or near the layer of interest, incident light may be generated at a shorter wavelength range for detecting defects in the layer of interest to achieve a strong detected signal in operation 205. For instance, a wavelength that is less than or equal to about 230 nm may be used to detect a signal from an area of interest that does not contain SiN. FIG. 1A shows that this range of 230 nm or less will result in a relatively strong signal for defects that are not in the presence of SiN, as compared to longer wavelengths. However, other shorter wavelengths ranges (e.g., below about 190 nm, below about 200 nm, below about 210 nm, or below about 220 nm) may be used. An even shorter wavelength range may be used, dependent on what wavelengths are available on the inspection tool.

However, if there is SiN present, it may then be determined whether the SiN is below the layer of interest in operation 206. If the SiN is below the layer of interest, incident light may be generated at a shorter wavelength range for detecting defects by achieving a strong response in signal strength, while also achieving a reduction of other noise sources from below the SiN due to the SiN being opaque at shorter wavelengths, in operation 205. For instance, the wavelength is set at below about 230 nm, 220 nm, 210 nm, 200 nm, or 190 nm (as illustrated in FIG. 1B).

If the SiN is not below the layer of interest, it may then be determined whether the SiN is positioned above the layer of interest or within the layer of interest in operation 207. If the SiN is in the layer of interest (or the layer of interest is comprised of SiN), incident light may be generated at both a narrow and shorter wavelength range for detecting defects in the layer of interest to achieve a strong detected signal in operation 208. For instance, the wavelength range is selected to be between about 230 nm and 250 nm, such as shown in FIG. 1C for SiN. If SiN is above the layer of interest, incident light may be generated at a longer wavelength to achieve a stronger detected signal for a defect that is below the SiN in operation 210. For example, the selected wavelength is greater than about 230 or 240 nm, above which SiN becomes transparent as illustrated in FIG. 1B.

If SiN is below the defect, then the light is generally absorbed, rather than possibly reflected, which will lower the electric field at the defect location. If SiN is adjacent to or above the defect, the SiN will also absorb the light incident on the wafer's surface and this arrangement will also tend to lower the electric field at the defect site. Accordingly, any SiN near the defect location generally results in a lower signal at wavelengths where SiN is absorbing.

Different wavelength ranges may also be selected to inspect different levels within a semiconductor stack structure, such as a vertical NAND (VNAND) or other 3D structure. For example, incident light having a shorter wavelength range (e.g., a red-visible, ultraviolet and/or a deep ultraviolet range) is used to detect defects on a surface of the 3D structure. Incident light having a higher wavelength range (e.g., a blue-visible, infrared, and/or near infrared range) is used to detect defects on both the surface and throughout a depth of the vertical stack. In a specific example, longer wavelengths are between about 700 and 950 nm and shorter wavelengths are between about 190 to 450 nm. The defects detected using the first and second wavelength range may be compared to obtain defects only throughout the depth of the 3D structure, excluding defects on the surface.

A polarization setting may also be applied to the longer or shorter wavelength range. For instance, a horizontal or vertical polarization may be selected for the selected wavelength range. A polarization setting may be applied based on any suitable inspection parameter, such as defect type, sample composition, wavelength range or sub-band selection, etc.

An aperture setting may also be applied to the shorter and/or longer wavelength range. For instance, an aperture setting for achieving a particular set of angles of incidence (AOI's) may be selected based any suitable inspection parameter, such as defect type, sample composition, type of sample structure being inspected, polarization setting, wavelength range or sub-band selection, etc.

Referring back to FIG. 2, the output light that is reflected and/or scattered from the layer of interest at a plurality of positions may be detected in operation 212. The output light may be used to generate digitized signals or images in operation 212. For example, each wafer may be scanned relative to the illumination beam to obtain images for entire swath portions of the wafer. In order to obtain a signal or image from each location, the wafer may be moved relative to the beam column; the beam column may be moved relative to the wafer; or the beam column and wafer may both be moved relative to each other. The resulting image swaths may be broken into image patches that are individually analyzed in parallel or serially. Although all the patches of a wafer would be typically inspected with a single selected wavelength, an alternative approach may include inspecting each patch or set of patches with a selected wavelength setting, which is dependent on the particular SiN characteristics of such patch. Polarization and aperture setting may also be applied to the collected light.

The output signals or images may then be analyzed to determine whether the any positions have a defect in operation 214. The generated signals or images may be analyzed in any suitable manner using any suitable technique. By way of examples, a die-to-die, cell-to-cell, or die-to-database technique may be used to inspect the sample. That is, defects may be detected for an imaged test area that may differ from another reference image area, which is free of defects and obtained from another die, cell, or simulated from a design database. A defect may be flagged when a difference between a test and reference image area is more than a predefined threshold value, which may vary based on desired sensitivity levels for different pattern types or locations on the sample.

In one embodiment, the design database (that was used to fabricate the reticles and wafer under test) is used to create reference optical images of the areas that are being imaged. In general, these reference images are rendered by simulating the reticle fabrication process and photolithography process to simulate wafer patterns. The inspection tool's physical configuration and optical characteristics (e.g., wavelength range, illumination and optical lens configurations, aberration effects, etc.) are also simulated to generate simulated wafer pattern images. In another embodiment, actual identical areas of an identical die or cell may be imaged with the inspection tool and used as reference areas to be compared to the test areas of a corresponding identical die or cell. Shorter wavelengths provide improved resolution and contrast so as to improve the comparison process for the die-to-database rendered images and tool images.

Defects on a sample may be repaired, or the sample may be discarded. A process for fabricating a next sample may be adjusted to minimize defects if the source of such defect can be determined. For instance, certain defect signatures may be associated with certain process conditions or issues during wafer fabrication, and such conditions or issues may be adjusted or corrected when such defect signatures are found on a wafer.

Certain embodiments enable wafer defect detection for the next generation design rules (DR) through use of shorter wavelength and flexible band selection to improve defect signal, inspection throughput, defect characterization, and nuisance reduction. An inspection tool with a broad range of wavelengths may be set up to have a different wavelength ranges for inspecting different wafer z planes (e.g., in a 3D stack structure). This flexible setup will allow the most complete inspection coverage. Also, the additional information in the detected signal and different tool settings can be used for defect classification and/or nuisance suppression.

Any suitable inspection system may be implemented for inspecting various types of materials in both the presence and absence of an absorber type material, such as SiN. Certain inspector tool embodiments provide flexible wavelength selection in order to cover a vast range of wafer material properties. Additionally, the inspection tool is operable to provide shorter wavelengths and may include flexible polarization selection in order to obtain the best signal. The inspection system may also be operable to collect more information in one scan to improve the inspection throughput, defect classification, nuisance suppression. For example, a wavelength range that is less than about 230 nm (or lower) may be selected to block underlying noise sources and detect defects when the SiN material is not present or is present below the wafer layer structure. The system may be operable to generate light at any of the wavelength ranges described herein, as well as other wavelength ranges for other types of absorber type materials besides SiN, as well as 3D stack structures.

In general, an applicable inspection tool for implementation of techniques of the present invention may include at least one light source for generating an incident light beam at different wavelengths to detect defects in different material types, including both absorber and non-absorber type materials, as well as possibly defects that are located on a surface and/or at various depths of a vertical semiconductor stack. Such an inspection may also include illumination optics for directing the incident beam to the area-of-interest, collection optics for directing an output beam that is emitted from the area-of-interest in response to the incident beam, a sensor for detecting an output beam and generating an image or signal from the detected output beam, and a controller for controlling the components of the inspection tool and facilitating defect detection in various materials and on the surface and at various depths in a stack as described further herein.

In one embodiment, an inspection tool includes illumination and collection modules for generating and collecting light at longer wavelengths (above 230 nm-950 nm) and shorter wavelengths (190-230 nm). In a specific embodiment, the inspection tool generates and collects light in two wavelength ranges: near UV through a near infrared (NIR) or IR range and a deep ultraviolet (DUV) to near UV range. These wavelength ranges are not meant to be restrictive, and other ranges may be considered or applied to embodiments of the present invention. For instance, lower wavelengths (e.g., below 190 nm) may be used. SiN continues to become more absorbing below 190 nm so underlying noise will continue to be reduced at lower wavelengths. When design rules decrease, layer thickness tends to decrease as well so as to require more absorption in the material to keep the underlying noise low. The 190 nm range minimum may be selected for optics that can only support this lowest wavelength in a broadband implementation. The inspector tool may also provide polarization options for parallel and perpendicular e-field and a set of sub-band wavelength filters for applying across the wavelength range for each of the long and short wavelength paths.

Use of short and long wavelengths (either independently or simultaneously) allow the capture of (i) defects in the absence of an absorber material, such as SiN, (ii) defects in the presence of an absorber material below the layer of interest, (iii) defects in the presence of an absorber material in the layer of interest, (iv) defects in the presence of an absorber material above the layer of interest, (v) surface defects in a vertical stack structure with shorter wavelengths, (vi) both surface defects and buried defects in a vertical stack by the use of longer wavelengths, and (vii) only the buried defects in a vertical stack by using a difference of the shorter and longer wavelength defect reports.

Figure 3:
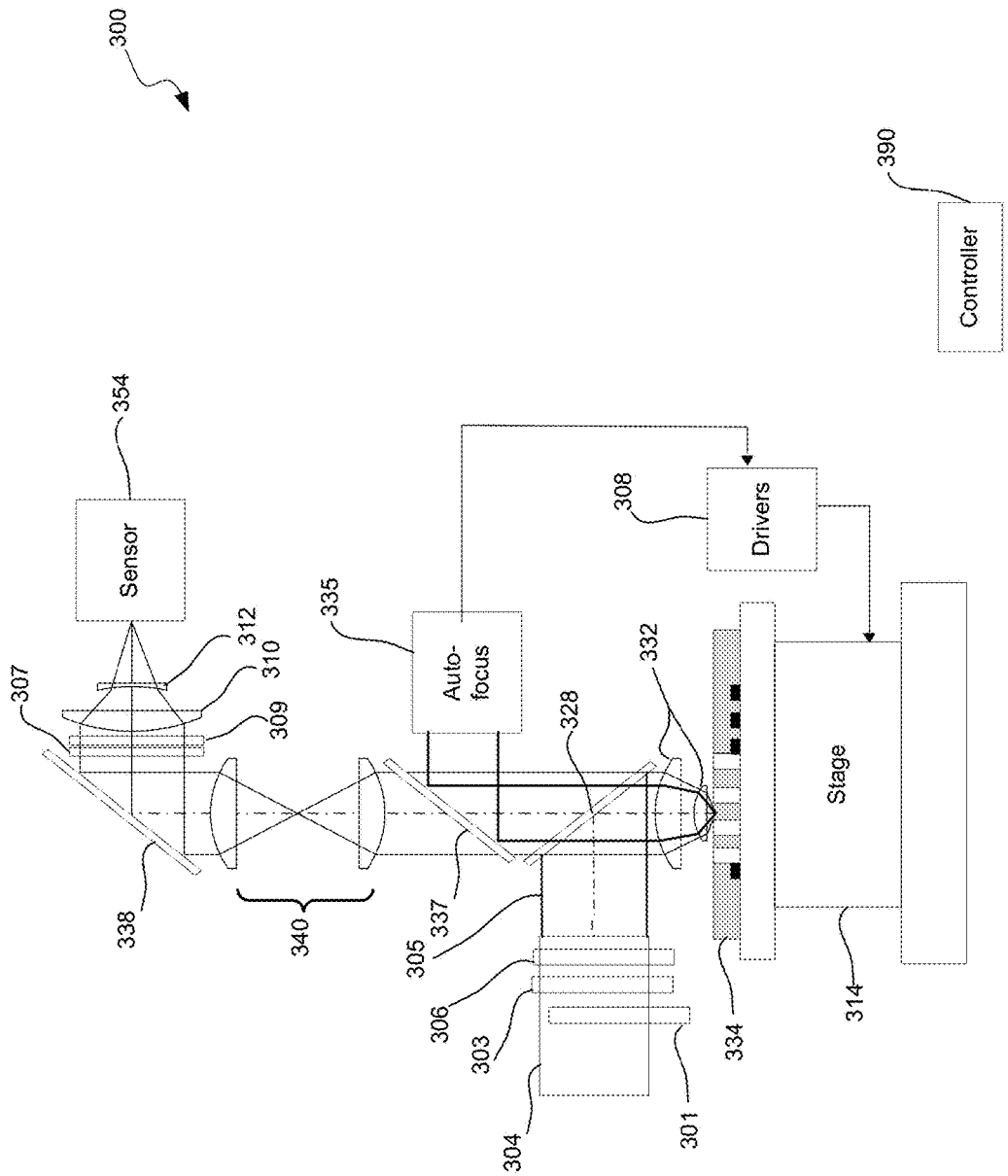
FIG. 3 is a diagrammatic representation of an example inspection system in accordance with a specific implementation of the present invention.

FIG. 3 is a diagrammatic representation of an example inspection system 300 in accordance with a specific implementation of the present invention. As shown, the system 300 includes a broadband light source (e.g., illuminator 304) which generates illumination light 305. Examples of light sources include a laser-driven light source, a high-power plasma light source, a transillumination light source (e.g., halogen or Xe lamp), a filtered lamp, LED light sources, etc. The inspection system may include any suitable number and type of additional light sources, besides broadband light sources.

The incident beam from the light source may generally pass through any number and type of lenses which serve to relay (e.g., shape, focus or adjust focus offset, filter/select wavelengths, filter/select polarization states, resize, magnify, reduce distortion, etc.) the beam towards a sample.

The illuminator 304 may include any suitable optical elements for generating an incident beam having a shorter wavelength range beam and a longer wavelength range beam. For example, the illuminator 304 may include a filter wheel 301 with selectable bandpass filters that are individually selectably inserted (or rotated) into the illumination path to change the wavelength of the illumination beam.

The shorter wavelength range may have a maximum that is less than about 230 nm (or less than about 200 nm, 210 nm, or 220 nm) for SiN or less than an absorption edge wavelength for another particular absorber type material. The longer wavelength may be greater than about 210, 220, or 230 nm. The minimum value of the shorter wavelength is optional, depending upon the nature of the inspector system and costs. Generally, each inspection wavelength range may also be selected based on optimization of its illumination and collection pupil aperture shapes, polarization of the incident and collection path, magnification, pixel size, or any combination thereof.

The illuminator may also include one or more additional spectral filters 303) that may be used to further define the spectrum of the incident beam. For example, each spectral filter can further be used to optimize the sensitivity for the defects that are intended to be captured. A separate polarizing filter 306 can also be selectively positioned in the incident beam path to further optimize the inspection sensitivity for particular wavelength ranges. For example, horizontal polarization (as well as longer wavelengths) may be selected for penetration into vertical trenches of thick stacks. The polarizing filter may also include a vertical polarization setting.

A pupil relay (not shown) may also be used to reimage the incident light and focus the pupil onto the system pupil at the objective lens 332. A 50-50 beam splitter 328 may be used to send the light to the objective lens 332. The 50-50 beam splitter 328 may also be arranged to send light reflected or scattered from the sample toward collection optics. A pupil that is conjugate to the system pupil (located at the objective lens) may be used in the incident beam path. Each pupil or aperture can have a specific shape to obscure parts of the light path to maximize the signal for that particular wavelength range.

The objective lens 332 is preferably optimized for all of the wavelengths that are used for defect detection. For instance, the objective 332 has a composition, including lens coatings, and arrangement for correction of color aberration. In an alternative embodiment, the objective lens 332 may be an all reflective objective or refractive or a combination (catadioptric) configuration.

The resulting output beam reflected or scattered from the sample may then be received by another dichroic beam splitter 337, which may be arranged to insert an autofocus into the objective lens 332 via auto-focus system 335. The autofocus beam may have a wavelength that is separated from the different inspection bands. The wavelength for the autofocus can be varied as long as it is not in the inspection wavebands for any of the shorter or longer wavelength ranges, and it does not necessarily need to be in between the inspection bands. Cost and availability of components can affect where the auto-focus insertion is located.

In one embodiment, the autofocus wavelength is between the longer and shorter wavelength ranges. Alternatively, the autofocus wavelength may be above both the longer and shorter wavelength range. The autofocus wavelength band may be 40 nm or less to minimize focus plane change due to wafer material response. For instance, the auto-focus system 335 may use an LED light source. The dichroic beam splitter 337 may be arranged to reflect the autofocus waveband and transmit all light above and below that region. The 50-50 beam splitter 328 can also be configured to pass the autofocus light with high efficiency (e.g., by use of a coating). This element may improve the light efficiency of the auto-focus by nearly 4×.

If the autofocus wavelength is much higher than both the longer and shorter wavelength ranges, the autofocus beam will be affected by different thermally induced focus change than the inspection imaging system. The system may include mechanisms to provide feedback on the focus change due to environment (temperature, pressure), lens heating, etc. By way of examples, the auto-focus system 335 may include feedback mechanisms in the form of temperature and pressure sensors and a calibration wafer installed on the side of the wafer chuck for evaluating the focal plane change. Based on feedback, the auto-focus system 335 may adjust one or more of the lens elements (such as by moving lenses to form an adjustable air gap) to introduce focus correction. The frequency of the correction can also be determined based on such feedback.

The output beam may be directed and shaped by any suitable number and type of collection optics, such as pupil relay (lens group 340) and, mirror 338, a polarizer 307, aperture 309, and optics elements 310 and 312 for zooming and focusing the output beam onto sensor 354. By way of example, the sensor 354 may be in the form of a CCD (charge coupled device) or TDI (time delay integration) detector, photomultiplier tube (PMT), or other sensor.

The pupil relay 340 may be designed to form an image of the system pupil (at the objective lens 332) for the purpose of inserting specific apertures (309) in the collection path so as to optimize the inspection sensitivity for each wavelength range. Different aperture settings may be selected so as to achieve different angles of incidence on the sample. A polarizing filter (306 or 307) may be positioned in the illumination or collection path for the purpose of also optimizing the inspection sensitivity.

The long wavelength band pass may be between about 230 nm and 950 nm and the short wavelength may be less than about 230 nm. Sub-band spectral filters (not shown) can be used to optimize the inspection sensitivity for either the buried defects in the long wavelength path or for surface defects, such as particles, in the short wavelength path.

In another system embodiment, two simultaneous shorter and longer wavelength paths are produced. Such a simultaneous wavelength system may be used to locate defects in a 3D vertical stack structure, as well as accounting for the presence or absence of absorbing type materials. As further described above, incident light having a shorter wavelength range (e.g., a red-visible, ultraviolet and/or a deep ultraviolet range) is used to detect defects on a surface of the 3D stack structure, while incident light having a longer wavelength range (e.g., a blue-visible, infrared, and/or near infrared range) is used to detect defects on both the surface and throughout a depth of the vertical stack. Further spectral selection can be used for locations having SiN or Poly Si.

Figure 4:
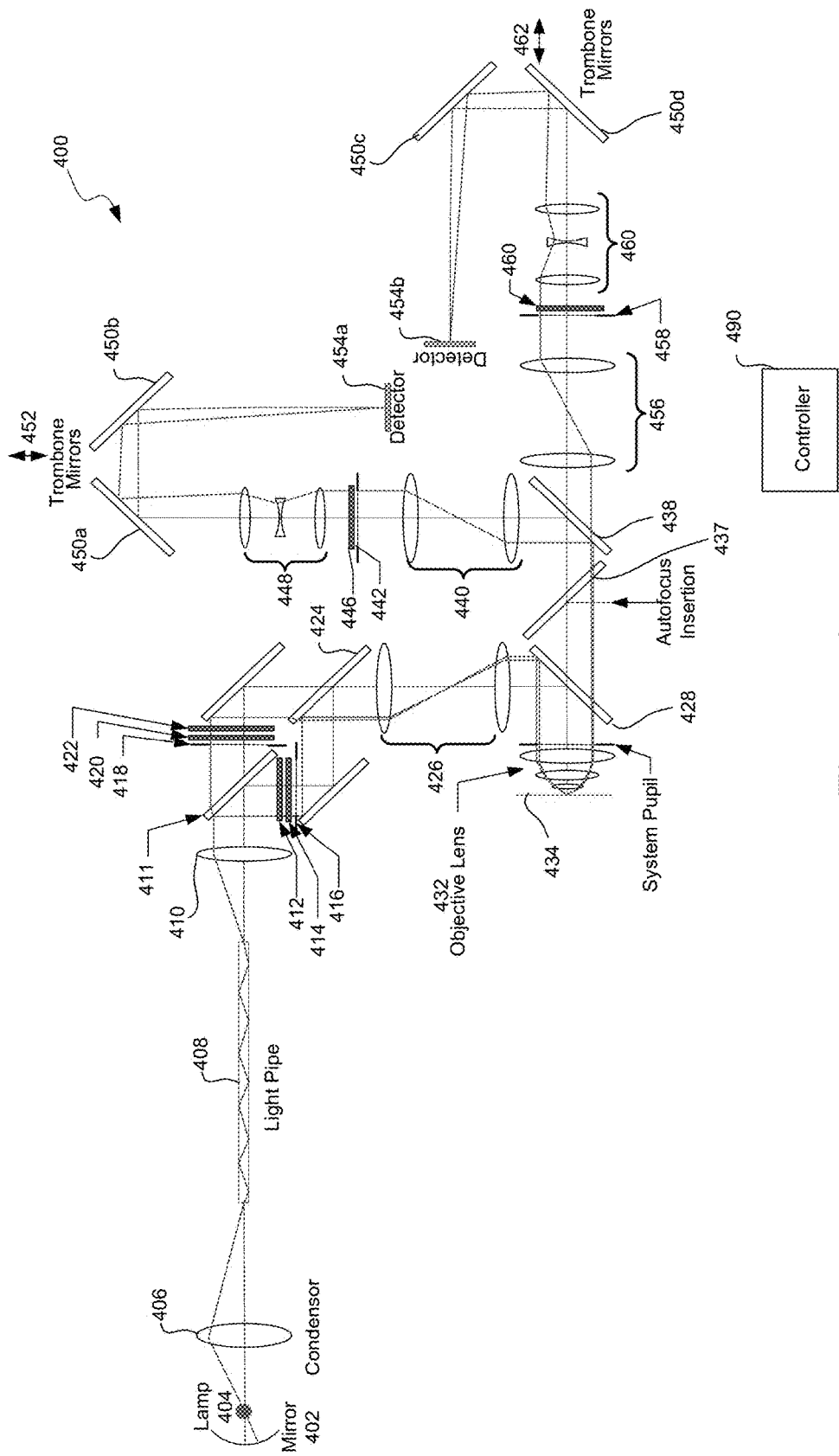
FIG. 4 is a diagrammatic representation of another example inspection apparatus in accordance with an alternative implementation of the present invention.

FIG. 4 is a diagrammatic representation of an example inspection apparatus in accordance with a specific implementation of the present invention. This system's components may be similar to components as described with respect to FIG. 3. Example systems that produce two different wavelength illumination beams are further described in U.S. Pat. No. 9,075,027, issued 7 Jul. 2015 by Steven R.

Lange, which patent is incorporated herein by reference in its entirety for all purposes. This patent also describes a system using two simultaneous illumination and collection wavelength paths.

As shown in FIG. 4, the system 400 includes a broadband light source (e.g., Xe arc lamp 404) which is directed and focused via mirror 402 and condensor lens 406 into light pipe 408. The light pipe generally homogenizes light. The homogenized light may then be received by lens 410, which collimates the received light.

The system 400 also includes optical elements for splitting the incident beam into a shorter wavelength beam that is directed along a shorter band path and a longer wavelength beam that is directed along a longer band path. The system 400 may include a dichroic beam splitter 411 for splitting the incident light into two different selectable wavelength band paths. In the illustrated system, a first wavelength path includes a first spectral filter 420 and first polarizer 422 positioned near a first illumination pupil 418. The second wavelength path includes a second spectral filter 414 and second polarizer 412 positioned near a second illumination pupil 416.

The dichroic beam splitter or filter 411 may be implemented in any suitable manner. For instance, dichroic prisms with dichroic optical coatings, which selectively reflect or transmit light depending on the light's wavelength, may be utilized in the system 400 to separate the incident beam into two separate wavelength paths.

Each spectral filter in each path spectrum may be used to further define the spectrum of each beam. For example, each spectral filter can further be used to optimize the sensitivity of each path for the defects that are intended to be captured or the presence or absence of an absorber material as described further above. A separate polarizing filter can also be positioned in each spectral path to further optimize the inspection sensitivity for each wavelength range. For example, horizontal polarization (as well as longer wavelengths) may be selected for longer wavelength ranges.

Each incident beam from the light source may also pass through a number of lenses which serve to relay (e.g., shape, focus or adjust focus offset, filter/select wavelengths, filter/select polarization states, resize, magnify, reduce distortion, etc.) the beam towards a sample. In the illustrated embodiment, the incident beams from the two wavelength paths are directed by illumination path optical elements, such as mirrors, and received by a dichroic beam splitter 424, which is arranged to recombine the incident beams from the two wavelength band paths. The recombined incident beam may then be directed by any illumination optics, such as pupil relay 426, a 50-50 beam splitter 428, and objective lens 432, onto the sample 434.

A pupil relay 426 may be used to reimage the combined light and focus each pupil onto the system pupil at the objective lens 432. A 50-50 beam splitter 428 may be used to send the light to the objective lens 432. The 50-50 beam splitter 428 may also be arranged to send light reflected or scattered from the sample toward the collection optics.

The objective lens 432 is preferably optimized for all of the wavelengths that are used for detect detection. For instance, the objective 432 has a composition, including lens coatings, and arrangement for correction of color aberration. In an alternative embodiment, the objective lens 432 may be an all reflective objective or refractive or a combination (catadioptric) configuration.

The resulting output beam reflected or scattered from the sample may then be received by another dichroic beam splitter 437, which may be arranged to insert an autofocus into the objective lens 432. The autofocus beam may have a wavelength that is separated from the two inspection bands. The wavelength for the autofocus can be varied as long as it is not in the inspection wavebands for either the short or long wavelength paths as described above.

The dichroic beam splitter 437 may be arranged to reflect the autofocus waveband and transmit all light above and below that autofocus region. The 50-50 beam splitter 428 can also be configured to pass the autofocus light with high efficiency (e.g., by use of a coating).

The dichroic beam splitter 437 may also be arranged to transmit the reflected or scattered output beam to another output dichroic beam splitter 438, which splits the output beam into longer and shorter wavelength band paths similar to the imaging wavelength bands.

The first output beam may be directed and shaped by any suitable number and type of collection optics, such as pupil relay and magnification lens 440, a polarizer 446 near pupil 442, zoom lens 448, and trombone mirrors 450a and 450b that are independently movable along direction 452. The first output beam is received by a first detector 454a. Likewise, the second output beam may be directed and shaped by any suitable number and type of collection optics, such as pupil relay and magnification lens 456, a polarizer 460 near pupil 458, zoom lens 460, and trombone mirrors 450c and 450d that are independently movable along direction 462. The second output beam is received by a second detector 454b.

Regardless of the particular system embodiment, each optical element may be optimized for the particular wavelength range of the light in the path of such optical element. For instance, optical elements in the shorter wavelength path are optimized for such shorter wavelength range, while optical elements in the longer wavelength range path are optimized for such longer wavelength range. Likewise, optical elements that are in the path of a combined shorter and longer wavelength range light are optimized for such combined wavelength ranges. Optimization may include minimizing wavelength-dependent aberrations, for example, by selection of glass type, arrangement, shapes, and coatings (e.g., anti-reflective coatings, highly reflective coatings) for minimizing aberrations for the corresponding wavelength range. For example, the lenses are arranged to minimize the effects caused by dispersion by shorter and longer wavelength ranges. In another embodiment, all the optical elements are reflective. Examples of reflective inspection systems and configurations are further described in U.S. Pat. No. 7,351,980 issued 1 Apr. 2008, which patent is incorporated herein by reference in its entirety.

The optical layout of the inspection tool can vary from that described above with respect to FIG. 3 or FIG. 4. For example, the system microscope objective lens can be one of many possible layouts, as long as the transmission coatings are optimized for the particular selected wavelength band or sub-band and the aberration over each waveband is minimized. Different light sources can be used for each path. For instance, a Xe source may be used for the long wavelength path and an HgXe or Hg lamp may be used for the short wavelength path. Multiple LED or speckle buster laser diodes are also possible sources for each path. The zoom can be modified to include different magnification ranges either via a lens-only approach, a mostly fixed lens with an optical trombone, or any combination thereof.

Certain inspection system embodiments can be configured for inspecting semiconductor structures. Other types of structures that may be inspected or imaged using the inspection apparatus of the present invention include solar panel structures, optical disks, etc.

The system may also include a controller or computer system (e.g., 390 or 490). For instance, the signals captured by each detector can be processed by controller 390, which may include a signal processing device having an analog-to-digital converter configured to convert analog signals from each sensor into digital signals for processing. The controller may be configured to analyze intensity, phase, and/or other characteristics of the sensed light beam. The controller may be configured (e.g., with programming instructions) to provide a user interface (e.g., on a computer screen) for displaying resultant test images and other inspection characteristics as described further herein. The controller may also include one or more input devices (e.g., a keyboard, mouse, joystick) for providing user input, such as changing wavelength, polarization, or aperture configuration, viewing detection results data or images, setting up an inspection tool recipe.

Techniques of the present invention may be implemented in any suitable combination of hardware and/or software. The controller typically has one or more processors coupled to input/output ports, and one or more memories via appropriate buses or other communication mechanisms.

The controller may be any suitable combination of software and hardware and is generally configured to control various components of the inspection system. For instance, the controller may control selective activation of the illumination source, the illumination or output aperture settings, wavelength band, focus offset setting, polarization settings, etc. The controller may also be configured to receive the image or signal generated by each detector and analyze the resulting image or signal to determine whether defects are present on the sample, characterize defects present on the sample, or otherwise characterize the sample. For example, the controller may include a processor, memory, and other computer peripherals that are programmed to implement instructions of the method embodiments of the present invention.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

As illustrated in FIG. 3, the sample 334 may also be placed on a stage 314 of the inspection system 300, and the inspection system 300 may also include a positioning mechanism 308 for moving the stage (and sample) relative to the incident beam. By way of examples, one or more motor mechanisms may each be formed from a screw drive and stepper motor, linear drive with feedback position, or band actuator and stepper motor. The one or more positioning mechanisms 308 may also be configured to move other components of the inspection system, such as illumination or collection mirrors, apertures, wavelength filters, polarizers, etc.

It should be noted that the above description and drawings of an inspection system are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

Any suitable lens arrangement may be used to direct the incident beam towards the sample and direct the output beam emanating from the sample towards a detector. The illumination and collection optical elements of the system may be reflective or transmissive. The output beam may be reflected or scattered from the sample or transmitted through the sample. Likewise, any suitable detector type or number of detection elements may be used to receive the output beam and provide an image or a signal based on the characteristics (e.g., intensity) of the received output beam.

For future wafer defect inspection, a defect signal is significantly reduced due to DR shrink. Therefore, since there is a general trend for achieving higher defect signals with decreasing wavelength, it is desirable to have shorter wavelengths, better resolution, and smaller inspection pixels. However, such a shorter wavelength inspection configuration can have the disadvantages of small depth of focus, high thermal sensitivity to focus change, lower throughput, etc. Certain system embodiments provide features to track & correct focus, adjust system parameters to optimize S/N, etc. In addition, this arrangement allows more information to be obtained in one scan to make inspection cost-effective. Also, by acquiring multiple information at one single scan, post processing for defect characterization, signal enhancement, and noise/nuisance reduction can be effectively performed.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. A method for inspecting semiconductor samples, comprising:
    on an inspection tool, selecting a plurality of different wavelength ranges for different layers of interest of one or more semiconductor samples based on whether such different layers of interest have an absorber type material present within or near such different layers of interest, wherein the absorber type material is $SiO_2$;

on the inspection tool, directing at least one incident beam at the different wavelength ranges towards the different layers of interest and, in response, obtaining a plurality of output signals or images for each of the different layers of interest; and analyzing the output signals or images from each of the different layers of interest to detect defects in such different layers of interest.

2. The method of claim 1, wherein selecting the different wavelength ranges comprises:

selecting a shorter wavelength range that is below an absorption edge wavelength of $SiO_2$ for a first one of the different layers of interest that does not have $SiO_2$ present within or near such first layer of interest or has $SiO_2$ present below such first layer of interest; and selecting a longer wavelength range that is above the absorption edge wavelength for a second one of the different layers of interest that has $SiO_2$ present above such second layer of interest.

3. The method of claim 2, wherein selecting the different wavelength ranges further comprises:

selecting a narrow and shorter wavelength range at a third one of the different layers of interest that has $SiO_2$ present within such third layer of interest.

4. The method of claim 3, wherein selecting the different wavelength ranges includes determining whether there is $SiO_2$ present within or near each of the different layers of interest as specified in a design database with which the sample was fabricated.

5. The method of claim 3, wherein selecting the different wavelength ranges includes determining whether there is $SiO_2$ present within or near each of the different layers of interest as specified with a list of layers and material type without provision of a design database with which the sample was fabricated.

6. The method of claim 3, further comprising applying a horizontal or vertical polarization to the at least one incident beam.

7. The method of claim 3, further comprising selecting different aperture settings for the at least one incident beam to achieve a particular angle of incidence for at least some of the different layers of interest.

8. The method of claim 1, wherein at least some of the different wavelength ranges for a particular layer of interest having a vertical stack structure include a longer wavelength range to detect defects on both a surface and throughout a depth of the vertical stack structure and a shorter wavelength range to detect defects on the surface of the vertical stack structure.

9. An inspection system for inspecting a semiconductor sample, comprising:

an illumination optics module for generating and directing an incident beam towards one or more semiconductor sample at a plurality of different wavelength ranges for different layers of interest based on whether such different layers of interest have an absorber type material present within or near a layer of interest at such different layers of interest;

a collection optics module for collecting an output beam that is reflected or scattered from the different layers of interest in response to the incident beam; and a controller that is configured to perform the following operations:

selecting a plurality of different wavelength ranges for different layers of interest of one or more semiconductor samples based on whether such different layers of interest have an absorber type material present within or near such different layers of interest, wherein the absorber type material is $SiO_2$;

causing at least one incident beam to be directed at the different wavelength ranges towards the different layers of interest and, in response, obtaining a plurality of output signals or images for each of the different layers of interest; and analyzing the output signals or images from each of the different layers of interest to detect defects in such different layers of interest.

10. The system of claim 9, wherein selecting the different wavelength ranges comprises:

selecting a shorter wavelength range that is below an absorption edge wavelength of $SiO_2$ for a first one of the different layers of interest that does not have $SiO_2$ present within or near such first layer of interest or has $SiO_2$ present below such first layer of interest; and selecting a longer wavelength range that is above the absorption edge wavelength for a second one of the different layers of interest that has $SiO_2$ present above such second layer of interest.

11. The system of claim 10, wherein selecting the different wavelength ranges further comprises:

selecting a narrow and shorter wavelength range at each of a third set of the different layers of interest that has $SiO_2$ present within such third layer of interest.

12. The system of claim 11, wherein selecting the different wavelength ranges includes determining whether there is $SiO_2$ present within or near each of the different layers of interest as specified in a design database with which the sample was fabricated.

13. The system of claim 11, herein selecting the different wavelength ranges includes determining whether there is SiN present within or near each of the different layers of interest as specified with a list of layers and material type without provision of a design database with which the sample was fabricated.

14. The system of claim 11, wherein the controller is further configured for applying a horizontal or vertical polarization to the at least one incident beam.

15. The system of claim 11, wherein the controller is further configured for selecting different aperture settings for the at least one incident beam to achieve a particular angle of incidence for at least some of the different layers of interest.

16. The system of claim 9, wherein at least some of the different wavelength ranges for a particular layer of interest having a vertical stack structure include a longer wavelength range to detect defects on both a surface and throughout a depth of the vertical stack structure and a shorter wavelength range to detect defects on the surface of the vertical stack structure.

* * * * *